United States Patent
Shahin-Shamsabadi (10) Patent No.: US 11,718,830 B1
(45) Date of Patent: Aug. 8, 2023

(54) SILICONE-BASED MEMBRANE SURFACE CHEMISTRY AND TOPOGRAPHY CONTROL FOR MAKING SELF-ASSEMBLED CELL SHEETS WITH CELL ALIGNMENT AND POSITIONING

(71) Applicant: CaroMeats Inc., Kitchener (CA)

(72) Inventor: Alireza Shahin-Shamsabadi, Kitchener (CA)

( * ) Notice: Subject to any disclaimer, the term of this patent is extended or adjusted under 35 U.S.C. 154(b) by 0 days.

(21) Appl. No.: 17/882,693

(22) Filed: Aug. 8, 2022

Related U.S. Application Data (63) Continuation of application No. 17/838,284, filed on Jun. 13, 2022, now abandoned.

(51) Int. Cl.
| | |
|---|---|
| C12N 5/077 | (2010.01) |
| B33Y 10/00 | (2015.01) |
| B33Y 40/00 | (2020.01) |
| B29C 64/118 | (2017.01) |

(52) U.S. Cl.
CPC ............ *C12N 5/0658* (2013.01); *B33Y 10/00* (2014.12); *B33Y 40/00* (2014.12); *B29C 64/118* (2017.08); *C12N 2500/12* (2013.01); *C12N 2513/00* (2013.01); *C12N 2533/20* (2013.01); *C12N 2533/30* (2013.01); *C12N 2533/70* (2013.01); *C12N 2535/10* (2013.01); *C12N 2537/00* (2013.01); *C12N 2537/10* (2013.01)

(58) Field of Classification Search
CPC .............. C12N 5/0658; C12N 2500/12; C12N 2513/00; C12N 2533/20; C12N 2533/30; C12N 2533/70; C12N 2535/10; C12N 2537/00; B33Y 10/00; B33Y 40/00; B29C 64/118
See application file for complete search history.

(56) References Cited

U.S. PATENT DOCUMENTS

| | | | |
|---|---|---|---|
| 5,776,787 A | 7/1998 | Schinstine | |
| 2021/0180012 A1 | 6/2021 | Yang | |
| 2021/0189327 A1* | 6/2021 | Selvaganapathy | ... C12N 5/0068 |

FOREIGN PATENT DOCUMENTS

| | | |
|---|---|---|
| CN | 106046700 A | 10/2016 |
| CN | 105504759 B | 4/2017 |
| IN | 201721015210 A | 11/2018 |
| KR | 102215710 B1 | 2/2021 |
| WO | 2018058135 A1 | 3/2018 |

OTHER PUBLICATIONS

Akther F, Yakob SB, Nguyen N-T, Ta HT "Surface Modification Techniques for Endothelial Cell Seeding in PDMS Microfluidic Devices" Biosensors, 2020,10(11),182 (18 pages); doi: 10.3390/bios10110182. (Year: 2020).*

Jang Y, Kim H, Jung J, Oh J "Controlled Thin Polydimethylsiloxane Membrane with Small and Large Micropores for Enhanced Attachment and Membranes", Jul. 3, 2022, 12, 688, 10 pages,PMID: 9315480), doi: 10.3390/membranes12070688. (Year: 2022).*

Min-Hsien Wu, "Simple Poly(dimethylsiloxane) Surface Modification to Control Cell Adhesion," Surface and Interface Analysis, Jan. 2009, 41(1), pp. 11-16.

Srivatsan Kidambi, et al., "Cell Adhesion on Polyelectrolyte Multilayer Coated Polydimethylsiloxane Surfaces with Varying Topographies," Tissue Engineering, 2007, 13(8), pp. 2105-2117.

Viraj Mehta, et al. "Facile Route for 3D Printing of Transparent PETG-Based Hybrid Biomicrofluidic Devices Promoting Cell Adhesion," ACS Biomater. Sci. Eng., 2021, 7(8), pp. 3947-3963.

George Stiubianu, et al.,"Modification of Water Sorption Capacity of Polydimethylsiloxane based Composites by Incorporation of Lignin," Materiale Plastice, Dec. 2011, 48(4), pp. 289-294.

Pin-Chuan Chen, et al., "Systematically Studying Dissolution Process of 3D Printed Acrylonitrile Butadiene Styrene (ABS) Mold for Creation of Complex and Fully Transparent Polydimethylsiloxane (PDMS) Fluidic Devices," BioChip Journal, 2021, 15, pp. 144-151.

Aslihan Gökaltun, et al., "Simple Surface Modification of Poly(dimethylsiloxane) via Surface Segregating Smart Polymers for Biomicrofluidics," Scientific Reports, 2019, 9, Article No. 7377, pp. 1-13.

Natasha Patrito, et al., "Spatially Controlled Cell Adhesion via Micropatterned Surface Modification of Poly(dimethylsiloxane)," Langmuir, 2007, 23(2), pp. 715-719.

Veli Ozbolat et. al. "3D Printing of PDMS Improves Its Mechanical and Cell Adhesion Properties," ACS Biomaterials Science & Engineering, 2018, 4(2), pp. 682-693.

Xiaohul Lv, et al. "A one-step tannic acid coating to improve cell adhesion and proliferation on polydimethylsiloxane," New J. Chem., 2020, 44(35), pp. 15140-15147.

Arda Özen, et. al. "Optimization of Manufacturing Parameters and Tensile Specimen Geometry for Fused Deposition Modeling (FDM) 3D-Printed PETG," Materials, 2021,14, 2556.

(Continued)

*Primary Examiner* — Aaron J Kosar
(74) *Attorney, Agent, or Firm* — Gearhart Law LLC; David Postolski (57) ABSTRACT

Systems and methods for creating cell sheets with high extracellular (ECM) content, while controlling cell alignment, are described. The method is simple, easy to perform, has a low-cost, and uses non-toxic and food-grade and food-safe materials. The method allows for cell alignment in sophisticated patterns using simple molding process with 3D printed molds prepared with cheap open-source 3D printers and using different types of filament materials. The method allows for the reuse of the silicone-based membranes by simple autoclaving and/or an isopropanol washing step. The method also creates multi-layer cell constructs and induced ECM production with optional ECM crosslinking using food-grade materials resulting in strong sheets formed in a short process that can be formed using simple scraping.

20 Claims, 11 Drawing Sheets

(56) References Cited

OTHER PUBLICATIONS

Ho Nam Chan, et. al. "Direct, one-step molding of 3D-printed structures for convenient fabrication of truly 3D PDMS microfluidic chips," Microfluidics and Nanofluidics, 2015, 19, 9-18.

Rodi Abdalkader, et. al. "The Development of Biomimetic Aligned Skeletal Muscles in a Fully 3D Printed Microfluidic Device," Biomimetics, 2022, 7, 2.

Tim Femmer, et. al. "Print your own membrane: direct rapid prototyping of polydimethylsiloxane," Lab on a Chip, 2014, 14(15), pp. 2610-2613.

Yon Jin Chuah, et. al. "Simple surface engineering of polydimethylsiloxane with polydopamine for stabilized mesenchymal stem cell adhesion and multipotency," Sci. Rep., 2016, 5, 18162.

* cited by examiner

SILICONE-BASED MEMBRANE SURFACE CHEMISTRY AND TOPOGRAPHY CONTROL FOR MAKING SELF-ASSEMBLED CELL SHEETS WITH CELL ALIGNMENT AND POSITIONING

PRIORITY CLAIM

This application is a United States continuation application having priority to U.S. utility application Ser. No. 17/838,284, filed, Jun. 13, 2022, all of which are hereby incorporated by reference in their entirety as if fully set forth herein.

FIELD OF THE INVENTION

The field of this invention relates to silicone-based membranes surface chemistry. More specifically, the field of this invention relates to silicone-based membranes surface chemistry and topography control for making self-assembled cell sheets with cell alignment and positioning.

BACKGROUND OF THE EMBODIMENTS

Silicone-based polymer family members, such as PDMS, has favorable features for cell culture related applications, including their transparency and ease of microscopy, non-toxic and inert nature both chemical and biological, as well as their gas permeability. On the other hand, their intrinsic hydrophobicity results in non-specific protein adsorption, conformation and denaturation, as well as inappropriate cell attachment, agglomeration, and detachment (Walsh, 2017).

Multiple methods have been proposed to enhance surface hydrophilicity and improve cell attachment of the silicone-based elastomers, such as PDMS. For example, some groups propose use of high energy plasma radiation, which is a fast method, but the created Si-hydroxyl groups are short lived and migration of molecules from the bulk of the material can neutralize its effect (Fritz, 1995). Further, this method is also not suitable for large-scale industrial applications.

Other groups have proposed use of covalent immobilization of extracellular matrix proteins on the surface of the PDMS as an example method. However, this method requires functionalization of the PDMS surface by salinization and addition of linkers, such as 1-ethyl-3-(3-dimethylaminopropyl)carbodiimide/N-hydroxysuccinimide (EDC/NHS), glutaraldehyde, and polymer brushes. These modifications require multi-step and complicated processes involving harsh and often toxic materials which could leave residues and the use of organic solvents that can swell PDMS and damage its surface features (Li, 2018).

As another example, some groups have proposed coating the PDMS with dopamine (Chuah, 2015). However, dopamine monomers are expensive, potentially toxic, and the dark nature of the coating interferes with microscopy. Other proposed methods of improving PDMS cell attachment include grafting with polyethylene glycol or PEG after plasma treatment (Sharma, 2007) and surface modification with Pluronic F68, poly-L-lysine, and fibronectin (Wu, 2009).

Further, polyphenols from natural plant sources have been suggested for coating other materials, including PDMS, through formation of metal-phenolic networks by using iron(III) chloride (Lv, 2020) or cupric acetate (Chakrabarty, 2017) in complicated buffers, such as Tris and their co-deposition with biopolymers, such as tannic acid. The present invention illustrates the possibility of using tannic acid alone with deionized water as its solvent and its bonding to PDMS surface or other silicone-based elastomers to enhance cell attachment. Similarly, lignin, another polyphenol biopolymer never used before for such applications, is shown in this instant application to exhibit similar performances at much lower concentrations. These coatings are stable and can withstand autoclaving and washing steps with organic solvents, such as isopropanol that can cause PDMS swelling.

Moreover, cell sheet engineering was originally introduced in 1990s using cell culture surfaces, tissue culture polystyrene in particular, grafted with N-isopropylacrylamide (PIPAAm), a temperature sensitive material that allows for detachment of cells and their secreted extracellular matrix (ECM) proteins without using enzymes, such as trypsin that digest and destroy ECM proteins, to release the cells from the surface. This results in an intact cellular construct in the form of a sheet only by decreasing the temperature and changing the hydrophilicity of the grafted polymer (Yamada, 1990). Alternatively, other surfaces have been created for this purpose by layer-by-layer deposition of cationic and anionic polyelectrolytes on indium tin oxide (ITO) and the trigger for starting the delamination of cell sheets is lowering the pH as these layers become unstable at low pH and will not allow cell attachment (Guillaume-Gentil, 2011).

Another cell sheet formation technique includes growing cells on a feeder layer and detaching them by using another enzyme dispase that digests some of the ECM proteins and not cell-cell junctions. Growing cells on amniotic membrane as a carrier and then using them with the membrane has been used to make cell sheets, as well. Using surfaces sensitive to external stimuli such as light, electrochemical polarization, ionic solution, and magnetic force has also been used for making cell sheets (Owaki, 2014). A more recent technique that does not rely on characteristics of the surface for making cell sheets and uses slight changes in the pH of the environment to cause cells to show contraction and detach from the surface is only applicable to cells that show syncytialization and fusion such as skeletal muscle cells (Shahin-Shamsabadi, 2020). Thus, enhanced systems and methods for creating cell sheets with high ECM content, in a short time frame, while controlling different cells' positioning alignment, are needed.

Example Related Art Includes:

US20210180012A1 describes a method of fabricating curvature-defined (C-D) or shape-defined (S-D) convex and concave gel surfaces for use in cell and tissue culturing and in other surface and interface applications, and provides a method of using C-D or S-D convex and concave surfaces with varying curvatures to direct cell attachment, spreading, and migration.

U.S. Pat. No. 5,776,747A describes a method of derivatizing or adsorbing polyethylene oxide-poly(dimethylsiloxane) copolymer (PEO-PDMS) onto a surface within a bioartificial organ to inhibit cellular attachment.

KR102215710B1 describes a multilayer foam sheet of an acrylonitrile butadiene styrene (ABS) resin, which is a thermoplastic resin having excellent mechanical strength and low-temperature shock resistance, a manufacturing method thereof, and a three-dimensional (3D)-molded product manufacturing method using the sheet.

IN201721015210A describes a bio-inspired 3D-micro/nanofluidic device manufactured by a scalable fabrication process. The device comprises thin micro/nano vascularized membrane matrices made of PDMS or dimethicone.

WO2018058135A1 describes photocurable poly(siloxane) formulations for making stereolithographic 3D-printed PDMS structures, stereolithographic 3D-printing methods for making PDMS structures, and stereolithographic 3D-printed PDMS structures.

CN105504759B describes an ABS composite material used for 3D printing.

CN106046700A describes a method for preparing a 3D printing material from PETG plastic and a vegetable fiber.

Some similar methods and systems are known in the art. However, their means of operation are substantially different from the present disclosure, as the other inventions fail to solve all the problems taught by the present disclosure. For example, unlike CN105504759B, the present invention only utilizes 3D printing since it creates parallel patterns on the surface that can be mirrored to the PDMS membrane and may be used for cell alignment. Moreover, differing from IN201721015210A, the present invention casts PDMS to create a bulk and not porous membrane for cell culture. Further, the disclosure of KR102215710B1 provides an alternative method for using ABS for making molds instead of 3D printing, which is not used with a cell culture.

SUMMARY OF THE EMBODIMENTS

The present invention and its embodiments relate to systems and methods for creating cell sheets with high ECM content, while controlling cell alignment. It should be appreciated that the ECM is a three-dimensional (3D) network consisting of extracellular macromolecules and minerals, such as collagen, enzymes, glycoproteins and hydroxyapatite that provide structural and biochemical support to surrounding cells. These cell sheets can be made with any cell type from any species. The technique of the present invention is simple, easy to perform, has a low-cost, and can use non-toxic and food-grade and food-safe materials.

Further, the present invention allows for cell alignment in sophisticated patterns using simple molding processes with 3D printed molds prepared with cheap open-source 3D printers and using different types of filament materials. Similar patterns can be created on the mold using CNC machining or laser engraving on different materials. It is also possible to make the patterns directly on the membrane using CNC machining or laser engraving without the need to use a patterned mold. Moreover, the present invention provides for the reuse of membranes by simple autoclaving and/or an isopropanol washing step. Additionally, the present invention provides multi-layer cell constructs and induced ECM production with optional ECM crosslinking using food-grade materials resulting in strong sheets formed in a short process (usually ≤18 days) that can be formed using simple scraping.

An example embodiment described herein includes a method to create a cell sheet. The method includes numerous process steps, such as: treating a silicone-based membrane with an aqueous solution (e.g., an aqueous solution of tannic acid and/or an aqueous solution of lignin). In preferred examples, the silicone-based membrane is treated directly with about 50 mg/mL of the aqueous solution of tannic acid or about 1 mg/mL of the aqueous solution of lignin at room temperature for a time period of about 3 days. In some examples, the method also includes treating the surface of the treated silicone-based membrane with a solution (e.g., a sodium hydroxide solution in deionized water), plasma, or air atmosphere to improve a wettability of the surface of the silicone-based membrane.

Next, the method includes growing cells on the treated silicone-based membrane and aligning the cells on the treated silicone-based membrane. In some examples, the aligning of the cells on the treated silicone-based membrane occurs by creating patterns on a surface of the treated silicone-based membrane via lithography or by creating protein patterns on the surface of the treated silicone-based membrane. In other examples, aligning the cells on the treated silicone-based membrane occurs by utilizing three-dimensional (3D) printing to create a master mold with patterns that can be replicated to the treated silicone-based membrane by casting. In some implementations, the 3D printing comprises Fused Deposition Modeling (FDM) 3D printing. It should be appreciated that the patterns (e.g., a parallel pattern, a circular pattern, a concentric pattern, or a more complex pattern) are used as topographical signaling cues for the cells that are smaller to be aligned in certain directions. Further, the method includes creating a cell sheet.

In some examples, the method additionally includes: inducing the cells to produce a sufficient amount of extracellular matrix (ECM) by treating the cells with an ascorbate or adding a polyethylene glycol (PEG) or carrageenan to media. Next, the method may include: determining that the cells are confluent and have produced the sufficient amount of ECM. The method may also include growing additional cells on the initial cell-ECM layer. Next, the method may include cross-linking the ECM produced by the cells with tannic acid or lignin to create a stable structure and removing the cells and ECM of the cells from the surface of the silicone-based membrane to create the cell sheet. Removal of the cells and the ECM of the cells from the surface of the silicone-based membrane occurs by scarping the cells and the ECM of the cells off of the surface of the silicone-based membrane. In some examples, the method may include washing and autoclaving the treated silicone-based membrane to reuse the treated silicone-based membrane to grow new cells.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Overall Process

The present invention provides a method or process to create cell sheets with high extracellular (ECM) content, while controlling cell alignment. It should be appreciated that the cell sheets described herein can be made with any cell type from any species. The technique of the present invention is simple, easy to perform, has a low-cost, and uses non-toxic and food-grade and food-safe materials. Further, the present invention allows for cell alignment in sophisticated patterns using simple molding process with 3D printed molds prepared with cheap open-source 3D printers and using different types of filament materials. Similar patterns can be created on the mold using CNC machining or laser engraving on different materials. Moreover, the present invention provides for the reuse of membranes by simple autoclaving and/or an isopropanol washing step or a combination thereof. Additionally, the present invention provides multi-layer cell constructs and induced ECM production with optional ECM crosslinking using food-grade materials resulting in strong sheets formed in a short process (≤18 days) that can be formed using simple scraping.

A general method of the present invention includes three steps. First, the method includes growing cells on a treated silicone-based membrane, such as PDMS. PDMS treatment has been done with a variety of materials to make it suitable for cell culture, but these materials are usually expensive or toxic and require multistep treatments, including activation of the PDMS surface. To remedy this concern, the present invention utilizes direct treatment of PDMS with either a tannic acid solution in water or a lignin solution in water in order to make it suitable for cell attachment. It should be appreciated that both tannic acid and lignin is a food safe, natural, and non-toxic material. These PDMS treated membranes can be used for growing cells and/or can also be washed and autoclaved in order to reuse them for growing new cells. The treatment is stable and no re-treatment is required after autoclaving.

Second, the method includes aligning the cells on a surface of the treated membrane. Cells alignment on different membranes have been performed by creating micron or nanoscale features on the surface using lithography, or by creating protein patterns on the surface of the membrane. However, these processes are expensive, lengthy, and require specialized equipment. Some of the materials used in these processes can be animal-derived and therefore lower the consistency of the process. Distinctly, the present invention utilizes 3D printing with cheap and open-source printers, or alternatively CNC machining or laser engraving, in order to create meso-scale patterns that can be replicated to the silicone-based membrane by casting. This one step pattern creation on the membrane surface is enough to control cell alignment.

Third, the method includes cell sheet formation. Cells are grown and aligned on the membranes. They are induced to produce high amounts of ECM by using different growth factors and elements, such as ascorbic acid or by macromolecular crowding. Once the cells are completely confluent and have produced enough ECM, more cells are grown on this dense cell-ECM layer. In order to make a stable structure, the ECM can be crosslinked with low concentrations of tannic acid or lignin or other crosslinkers that can crosslink different ECM components such as transglutaminase. This can be repeated at least 3 times in a 2 to 3 week time span. At the end of the process, all of the cells and their ECM can be scraped off of the surface to make one coherent cell sheets in a short time. Other techniques for making cell sheets require either changing membrane properties to make it suitable for cell attachment, digesting some of the proteins that cells need for remaining attached to the surface, or inducing cells to show contraction that forces them to lift off. Distinctly, the present invention provides a cohesive multi-layer cellular construct that can be scrapped off using an external object. Among other benefits, the process described herein is simpler and shorter and can be used with any cell type from any species.

Membrane Fabrication

A method of fabricating a silicone-based membranes such as PDMS elastomers is also described herein. It should be appreciated that PDMS comprises an elastomer base and an elastomer curing agent. The method includes several process steps, such as: mixing the elastomer base and the elastomer curing agent at certain ratios (e.g., a 1:1 to 1:20 volume ratio of the curing agent to the base) and casting and heating the PDMS solution to cure the polymer and form the membrane. Methods of 3D printing may be used to print molds that are then used for casting the PDMS solution and creating the membranes. An example 3D printing method that may be used includes Fused Deposition Modeling (FDM) 3D printing. Patterns on the surface of the 3D printed molds may then be mirrored on the membrane. This may be leveraged to create patterns (e.g., parallel patterns) on the PDMS membrane that can be used for aligning the cells.

Different polymeric materials used with 3D printing for making the molds, as well as other techniques of creating patterns such as CNC machining or laser engraving, may create different resolutions that can have different effects on cell alignment. Other methods can also be used with nonpolymeric materials such as metallic ones. For example, the present invention contemplates use of thermoplastic polymers, such as PETG and ABS. However, it should be appreciated that other polymers may be used that are not explicitly listed herein. Further, it should be appreciated that Applicant further contemplates treating the ABS molds with acetone vapor to melt the polymer and change the resolution of the 3D printed part and consequently change the smoothness of the patterns on the membrane. It should be appreciated that timing of the treatment defines a final pattern.

According to the present invention, treatment times ranged from about 0 minutes to about 30 minutes. When the molds are ready, the PDMS solution may be cast and heated at a temperature of about 60° C. for a time period of about 5 hours to allow the polymer to cure. It is possible to perform the heating process at higher temperatures and by doing so, less time is needed.

Figure 1:
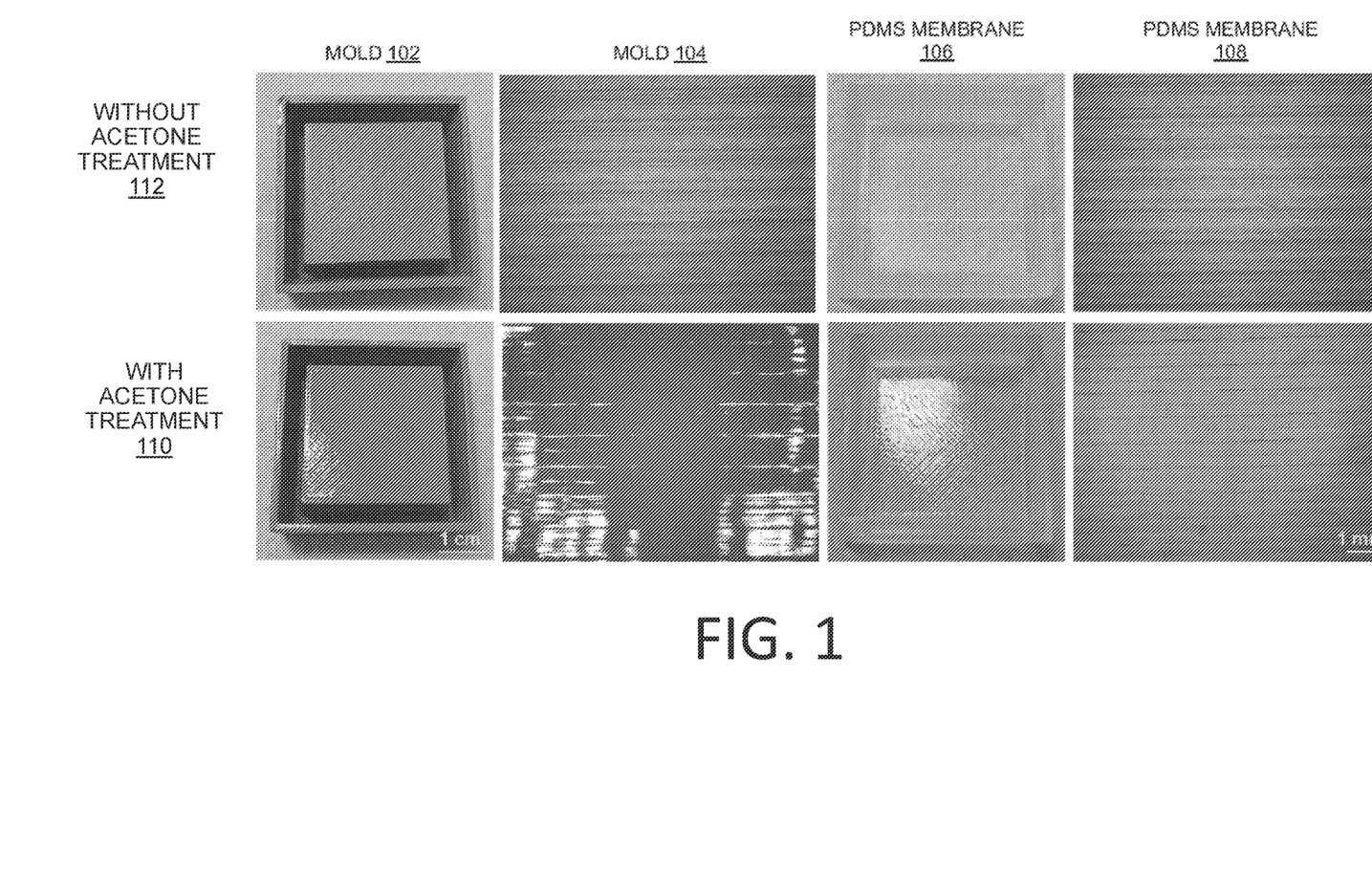
FIG. 1 depicts images of acrylonitrile butadiene styrene (ABS) master molds with and without an acetone vapor treatment, as well as polydimethylsiloxane (PDMS) membranes formed using the ABS molds, according to at least some embodiments disclosed herein.

FIG. 1 depicts images of ABS molds with and without an acetone vapor treatment, as well as PDMS membranes formed using the ABS molds, according to at least some embodiments disclosed herein. Specifically, FIG. 1 depicts a first row 112 associated with the ABS molds 102, 104 and the PDMS membranes 106, 108 formed using the ABS molds 102, 104 without the thirty-minute acetone vapor treatment and a second row 110 associated with the ABS molds 102, 104 and the PDMS membranes 106, 108 formed using the ABS molds 102, 104 with the thirty-minute acetone vapor treatment.

Figure 2:
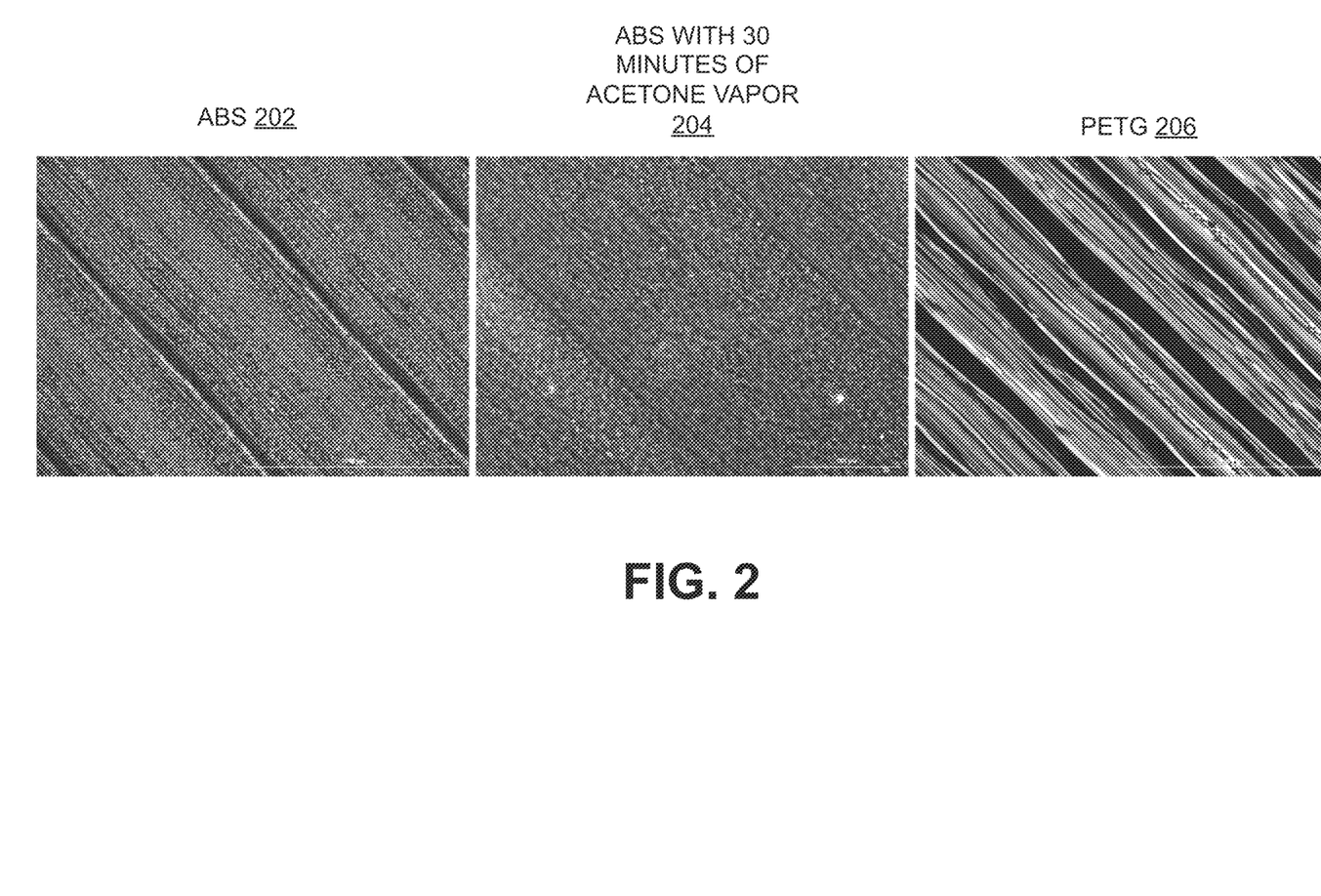
FIG. 2 depicts images showing an effect of a material (e.g., ABS, ABS with an acetone vapor treatment, or polyethylene terephthalate glycol (PETG)) used for 3D printing of a mold on the PDMS membrane formed by casting on the mold, according to at least some embodiments disclosed herein.

FIG. 2 depicts images showing an effect of a material (e.g., ABS 202, ABS with an acetone vapor treatment 204, or PETG 206) used for 3D printing of a mold, according to at least some embodiments disclosed herein. The present invention also contemplates creating complex patterns, such as circular or concentric patterns by controlling the pattern at which the material is deposited during the 3D printing process, such as the ones shown in FIG. 3, among others not explicitly listed or depicted herein.

Figure 3:
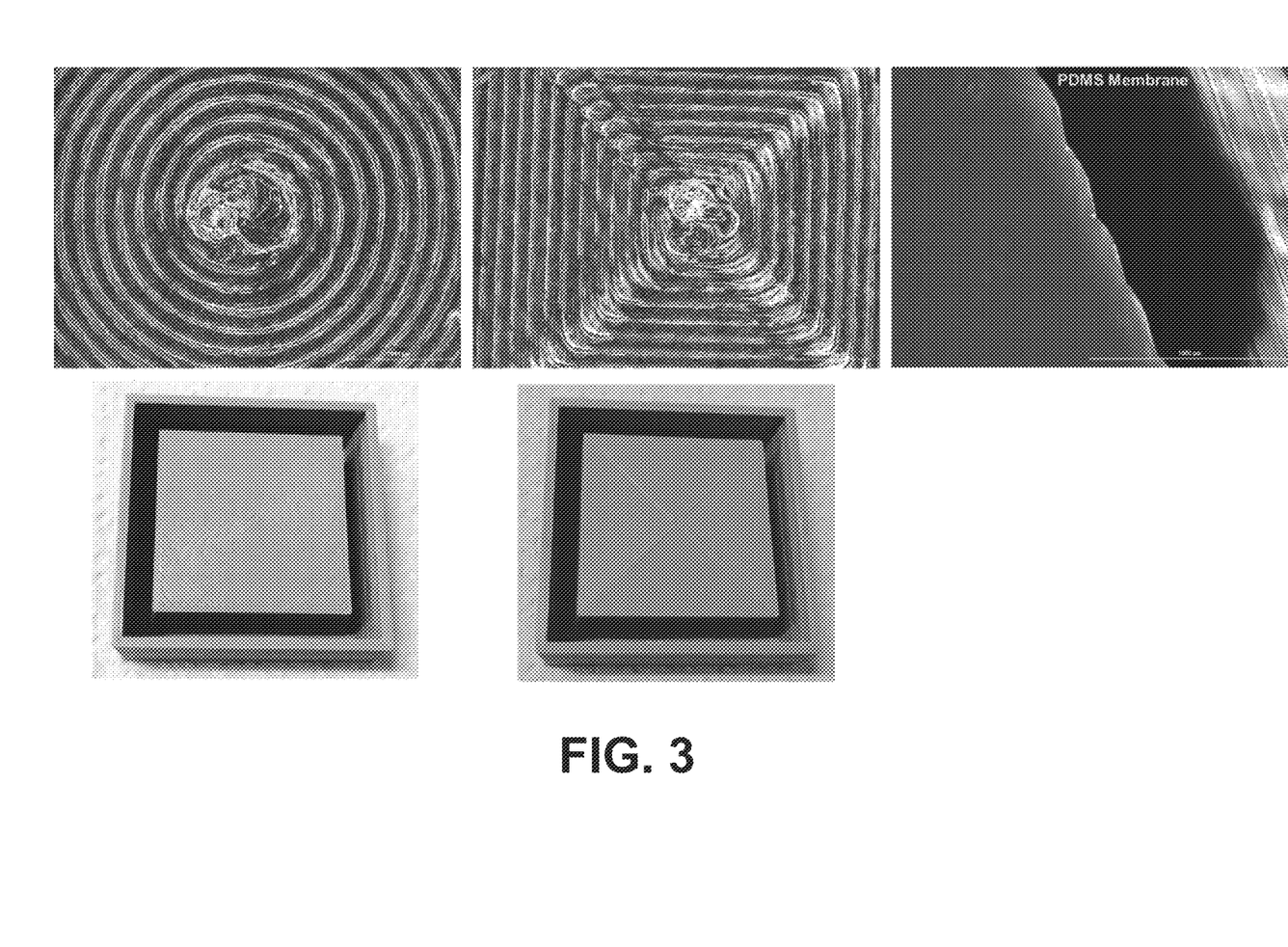
FIG. 3 depicts images showing complex patterns created on the PDMS membrane by controlling a pattern at which a material is deposited during a three-dimensional (3D) printing process, according to at least some embodiments disclosed herein.

It should be appreciated that independent of the pattern or material used for printing, the cross-section is always similar. Other methods and materials can also be used for making the molds as long as the size of the patterns is the same as what is created here using 3D printing, or sizes that can have similar effects on attachment and alignment of the cells. For example, CNC machining and laser ablation of different materials may be used to make similar molds. Furthermore, the molds can be made from metallic or polymeric materials, as well.

Treatment of Silicone-Based Membrane Surface for Cell Attachment

PDMS and other silicone-based membranes are hydrophobic materials and are not suitable for cell attachment, as such, the surface of PDMS requires chemical and/or physical modification to make it suitable for cell attachment. The present invention contemplates treating the surface of PDMS and other silicone-based membranes with an aqueous solutions of tannic acid or lignin are used for this purpose. In preferred embodiments, the conditions for such treatment include about 50 mg/mL of tannic acid or about 1 mg/mL of lignin at room temperature for a time period of about 3 days. It should be appreciated that lower or higher concentrations can be used for this purpose as well, but the timing of the treatment should be adjusted accordingly. In some embodiments, a solution containing both tannic acid and lignin can also be used.

In order to improve the absorbance of tannic acid and/or lignin to the surface of the membrane, the membrane can be pretreated with a sodium hydroxide solution in deionized water or plasma treated with oxygen or air atmosphere to improve its wettability. Once treatment with tannic acid and/or lignin is done, the present invention contemplates washing the membranes with deionized water at least twice to remove the residues. Then, the membranes may be used immediately for cell culture or can be stored at room temperature for a time period of a few weeks or in the refrigerator for a longer time period.

For sterilization purposes, before starting the treatment, the molds can be washed with about 70% ethanol and subjected to UV afterwards or they can be autoclaved. The tannic acid and/or lignin solutions can be sterile-filtered using about 0.2 μm syringe filters. The treatment may be done inside a biosafety cabinet to avoid possibility of contamination.

Figure 4:
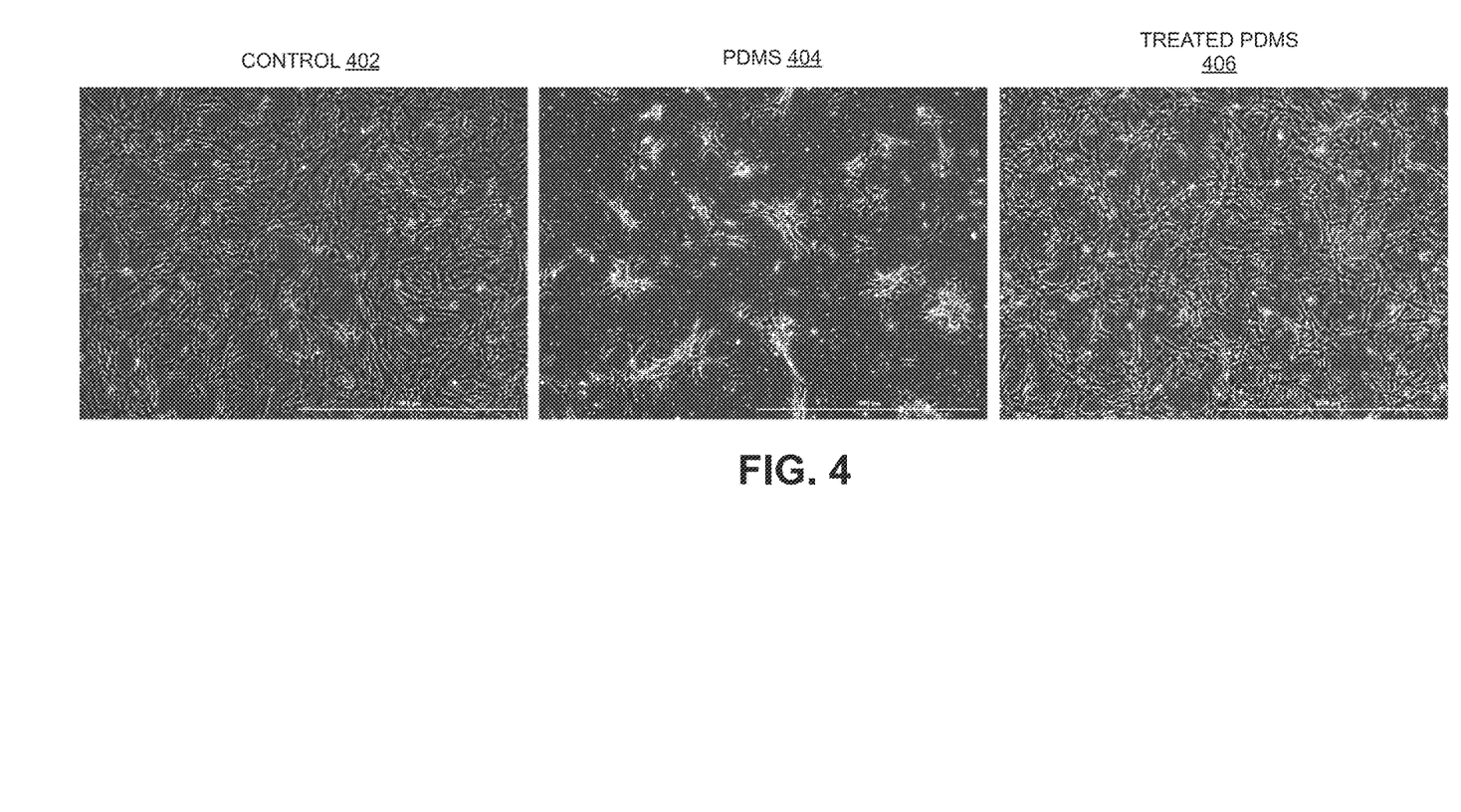
FIG. 4 depicts images showing the effect of treatment on cell attachment improvement between a PDMS membrane, a PDMS membrane treated with tannic acid or lignin solution, and cells grown in a control group, according to at least some embodiments disclosed herein.

FIG. 4 depicts images showing the effect of treatment on cell attachment improvement between a PDMS membrane 404, a treated PDMS membrane 406, and cells grown in a control group 402 (e.g., a commercially available cell culture treated polystyrene), according to at least some embodiments disclosed herein. As shown in FIG. 4, the PDMS membrane 404 without treatment does not allow for proper cell attachment and cells will either form agglomerates and clumps or will die. The membranes here don't have any patterns and as such cells are not aligned. If similar processes described previously are used here, such membranes can also be used for making cell sheets without any cell alignment.

Cell Alignment

Figure 5:
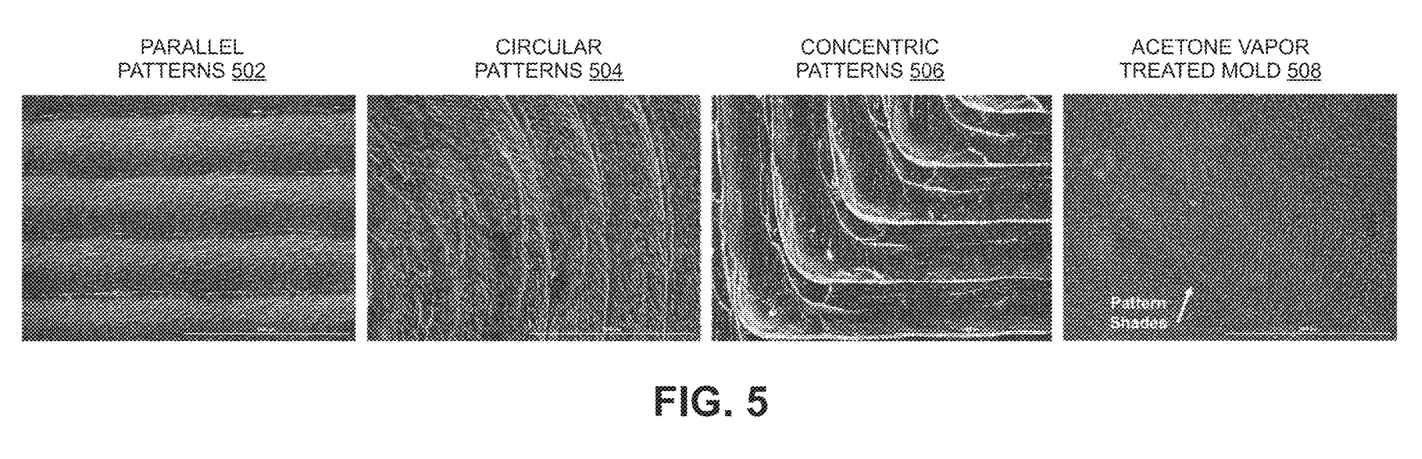
FIG. 5 depicts images of macro-scale patterns created by 3D printing using Fused Deposition Modeling (FDM) on the mold and transferred to PDMS membrane, and their effects on alignment of the cells grown on the PDMS membrane according to at least some embodiments disclosed herein.

It should be appreciated that 3D printing using FDM has a very low resolution and creates macro-scale patterns (up to a few hundred microns). Although these patterns can be considered as artifacts, they can be used as topographical signaling cues for cells that are much smaller to be aligned in certain directions, as shown in FIG. 5. Specifically, FIG. 5 depicts parallel patterns 502, circular patterns 504, concentric patterns 506 and pattern shades of an acetone vapor treated mold 508. By controlling the pattern of printing in different locations of the mold, a membrane with different patterns in different locations can be created, which can then be used to pattern cells. An example of this is in the case of skeletal muscle tissue where all of the cells should be aligned to properly differentiate and form muscle fibers that are aligned with each other. As an illustrative example, rabbit primary myoblast cells are used for demonstration purposes in FIG. 5. In case of molds treated with ABS, treatment with acetone vapor for longer time periods (e.g., more than 30 minutes) can result in diminishing the patterns on the mold completely or to a degree that cells won't be able to understand them. As a result, cells still show proper attachment but without any alignment.

Cell Sheet Formation

As described herein, a "cell sheet" is a scaffold-free sheet-like construct made out of cells and the ECM that they have secreted. Cell attachment to each other and to their ECM is preserved in each sheet and therefore each sheet can be maintained independent of a membrane or surface to adhere to. Since the ECM is preserved in each sheet, if multiple sheets are stacked on top of each other, they can bind and fuse to one another.

Further, the silicone-based membranes, with or without patterns, and treated with lignin and/or tannic acid, can be used for sheet formation in a simple process. The membrane provides a proper surface for cell adherence and cells form strong attachments to the PDMS membrane at the beginning. Over time, cells proliferate and start adhering to each other and form strong cell-cell junctions. They will also secrete their own ECM, which they will then adhere to.

As cells become more confluent and establish strong attachments to each other or their ECM, their attachment to the membrane weakens. Once the attachment of cells to each other and their ECM becomes stronger than their attachment to the membrane, cells and their ECM can be detached by a simple scraping method. It is also possible to make a cell sheet by scratching the edges of the membrane and shaking it to help cells delaminate as a sheet by applying shear force. It should be appreciated that the sheets are also strong enough to be grabbed and pooled off of the surface using a tweezer or similar means. Once peeled off from the surface, cells will maintain their alignment due to the high density of the cells and high ECM content in the sheets that prevents them from changing their alignment.

Once the cells cover an entire surface of the membrane and produce ECM, it is also possible to add more cells in order to grow on the initial layer of cells and create a multilayer construct. This can be performed multiple times to make a thicker construct, but if it is done more than a certain number of times, depending on the cell types and species up to 10 times, the attachment between cells of different layers becomes much stronger than attachment of the first layer to the membrane, which could result in uncontrolled detachment of the cells as one unit and their excessive shrinkage that turns the sheet into a clump.

Figure 6:
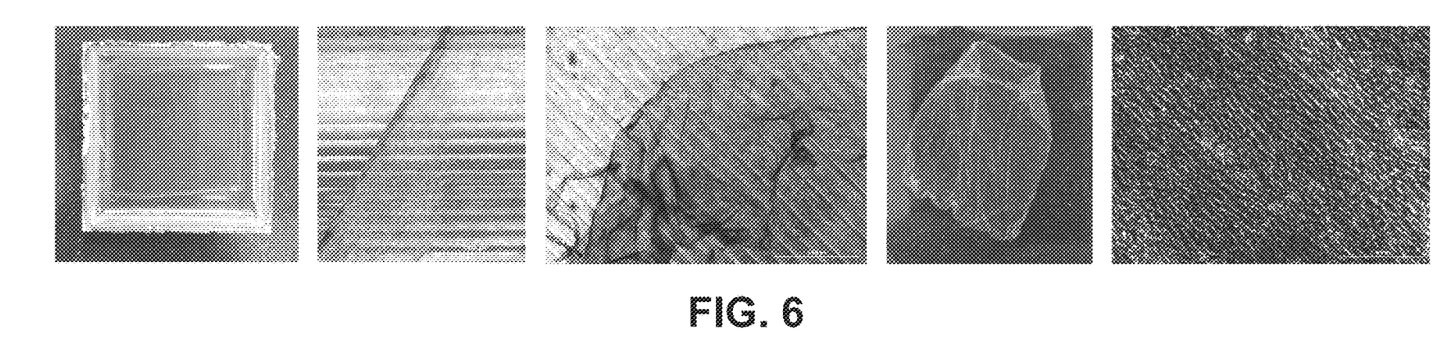
FIG. 6 depicts images showing different steps of sheet formation using the silicone-based membranes and preserved cell alignment in stand-alone cell sheets, according to at least some embodiments disclosed herein.

Further, it is possible to induce cells to secrete more ECM components by treating them with components, such as ascorbate family members, or by creating macromolecular crowding by addition of elements such as high molecular weight PEG or carrageenan with proper concentrations to the media. It is also possible to crosslink the ECM secreted by cells prior to addition of more cells to increase stability of the cellular constructs. Lower concentrations of tannic acid or lignin (e.g., about 0.01-10 µg/mL) in media can be used for crosslinking ECM components. The timing of treatment can be in a range from about 5 minutes to about 100 minutes depending on the crosslinker type and its concentration prior to addition of the new cells. Multiple cell layers, as well as more ECM content and crosslinking, can result in a sheet with better mechanical integrity that can help with handling the sheets and moving them from one vessel to another after delamination. Additionally, the present invention contemplates use of multiple cell types either in each layer or different cell types on different layers. For example, FIG. 6 depicts images showing different steps of sheet formation using the PDMS membranes and preserved cell alignment in stand-alone cell sheets, according to at least some embodiments disclosed herein.

Reusing Molds

Once a cell sheet is delaminated from the silicone-based membrane, all of the cells and a majority of their ECM is removed as well, but the membrane could allow unspecific penetration of certain smaller molecules to its bulk, which renders the membrane opaque. It is possible to first remove most of these components by submerging the membrane in deionized water and autoclaving the membrane for a time period of about twenty minutes. To further remove such residues, after autoclaving is performed, the membrane may be submerged in isopropanol or other non-polar solvents that can cause swelling in PDMS or other silicone-based membranes for a time period of about thirty minutes. The solvent will swell the membrane and the rest of these residues may be removed. At this point, the membrane can be used for cell culture again without repeating the treatment with tannic acid and/or lignin.

Figure 7:
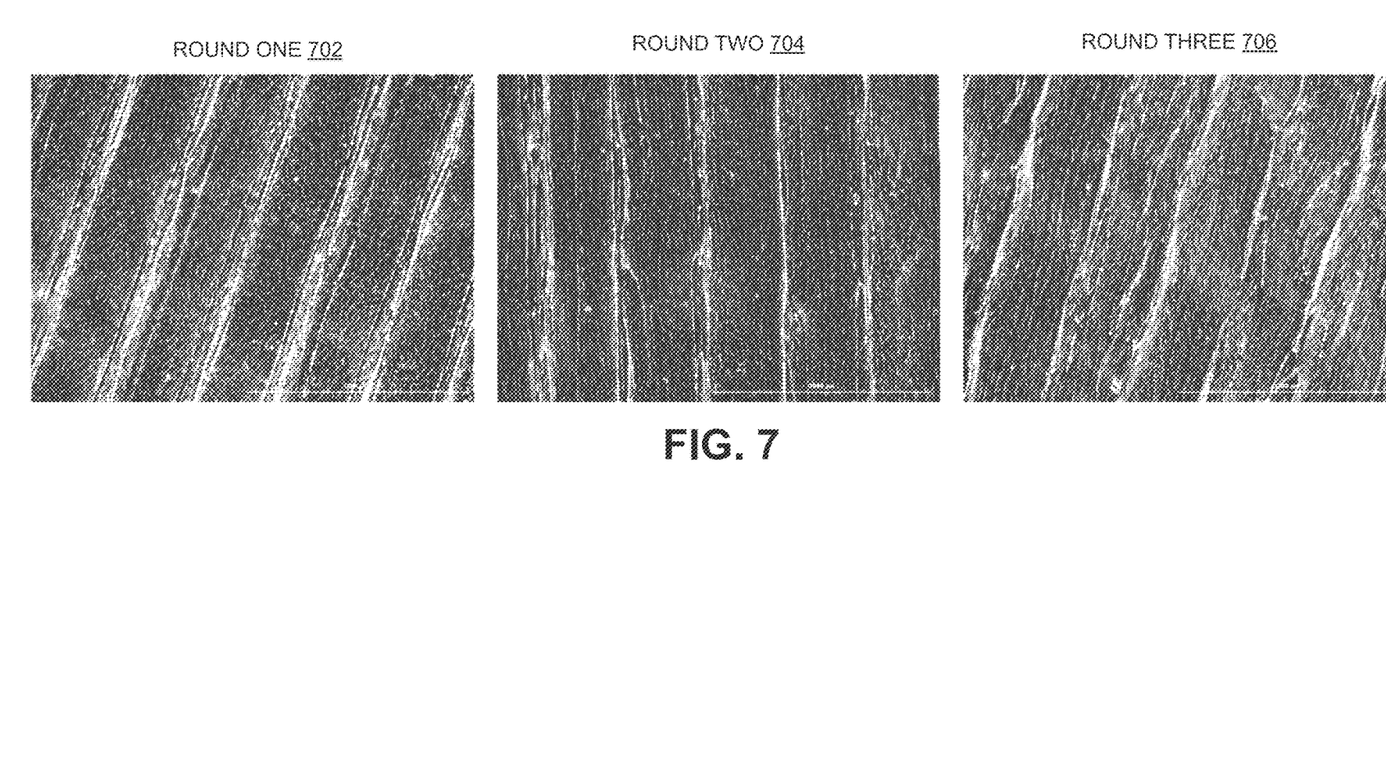
FIG. 7 depicts images of a PDMS membrane used for cell culture and reused for three times after being autoclaved and washed, according to at least some embodiments disclosed herein.

As an illustrative example, FIG. 7 depicts images of a PDMS membrane used for cell culture and reused for three times, round one 702, round two 704, and round three 706, according to at least some embodiments disclosed herein. There are no apparent differences between cell attachment, growth, differentiation or alignment. Further, rabbit myoblasts were grown and differentiated to muscle fibers on the PDMS membrane for a time period of about 8 days in each round (e.g., the round one 702, the round two 704, and the round three 706).

Cell Types

Figure 8:
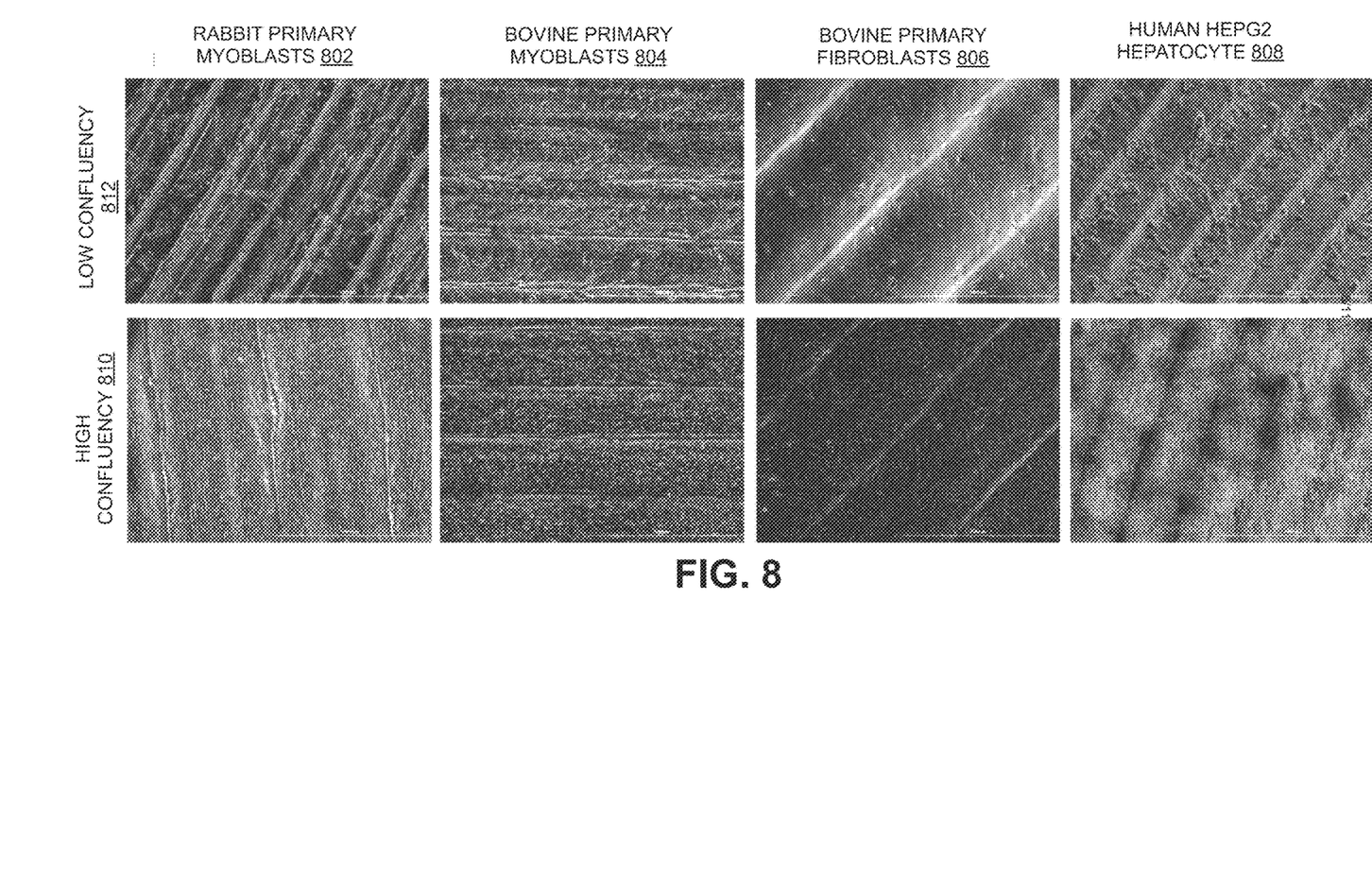
FIG. 8 depicts images of rabbit primary myoblasts, bovine primary myoblasts, and human HepG2 hepatocytes grown on treated PDMS membrane at both low and high confluency, according to at least some embodiments disclosed herein.

The tannic acid/lignin treated PDMS membranes with/without patterning can be used for growing different cell types from different tissues of different species, for both primary and immortalized cells. FIG. 8 depicts images of rabbit primary myoblasts 802, bovine primary myoblasts 804, bovine primary fibroblasts 806, and human HepG2 hepatocytes 808 at both low confluency 812 and high confluency 810, according to at least some embodiments disclosed herein. Different stem cells such as adult stem cells, embryonic stem cells, or induced pluripotent stem cells can be used in the process as well. The stem cells can also be differentiated to the target cells while grown and maintained on these membranes by switching the culture medium from growth medium to proper differentiation medium. As described herein, "confluency" is the percentage area covered by adherent cells. This measurement is routinely used to monitor cell growth and expansion during cell culture experiments. It is key in determining the optimal timings for cell harvest, passage and process interventions such as drug treatment or cell differentiation.

Specifically, according to FIG. 8, myoblasts that have elongated spindle-shaped morphologies from both rabbit and bovine sources (e.g., the rabbit primary myoblasts 802 and the bovine primary myoblasts 804) showed alignment in accordance with the membrane patterns, while bovine fibroblasts (e.g., the bovine primary fibroblasts 806) maintained their flattened morphology. Hepatocytes with round morphology (e.g., the human HepG2 hepatocytes 808) also maintained their shape independent of the membrane patterns.

Assembly of Sheets

Figure 9:
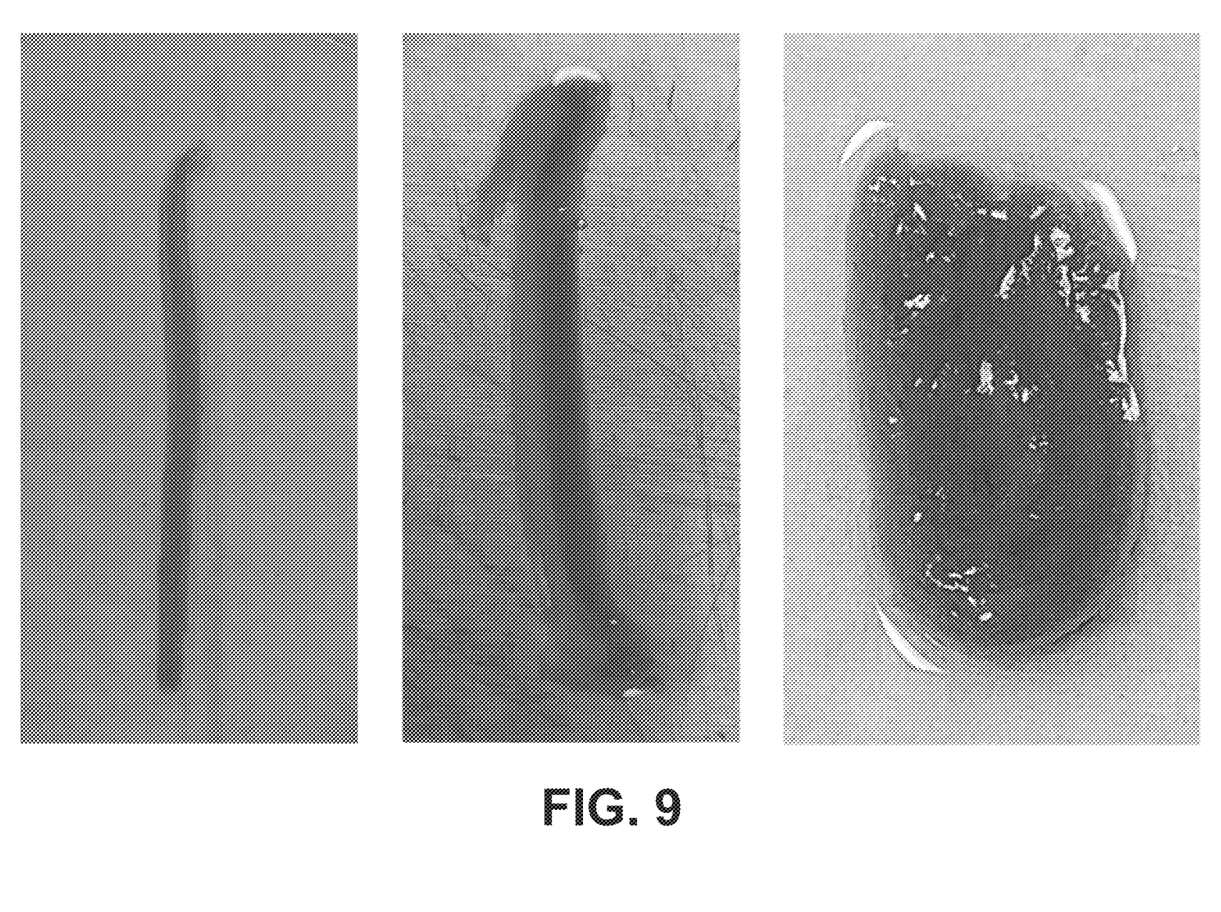
FIG. 9 depicts images showing creation of multiple cellular fibers from sheets that are stacked on top of each other and are adhered to one another, according to at least some embodiments disclosed herein.

Further, according to the present invention, the cell sheets can be rolled on themselves, and preserved ECM will result in formation of a coherent cellular structures that cannot be unrolled. Multiple cellular fibers made out of sheets can be stacked on top of each other, and they will also form firm attachment to each other, as shown in FIG. 9. If skeletal muscle cells are used, the rolling can be done in a direction that results in all of the muscle fibers aligned in the direction of the larger fiber. This functioning unit can be used for different applications, such as in vitro modeling of skeletal muscle tissue for drug discovery or modeling diseases, development of cultivated meat, as well as a building block for biofabrication of skeletal muscle tissue for regenerative medicine applications.

The present invention also contemplates creating cellular fibers with different cell types and stacking them. Examples of this application include creating marbling for cultivated meat by using skeletal muscle, adipose, and connective tissue derived cells, or creating more physiologically relevant models of different tissues and organs by recreating cellular crosstalk. Sheets stacked on top of each other without first rolling them, will also adhere to each other and form a coherent structure. An example of this includes making sheets of hepatocytes and stacking them to make liver-like tissue for either in vitro modeling or making foie gras as food.

Bioreactors for Dynamic Environment

Figure 10:
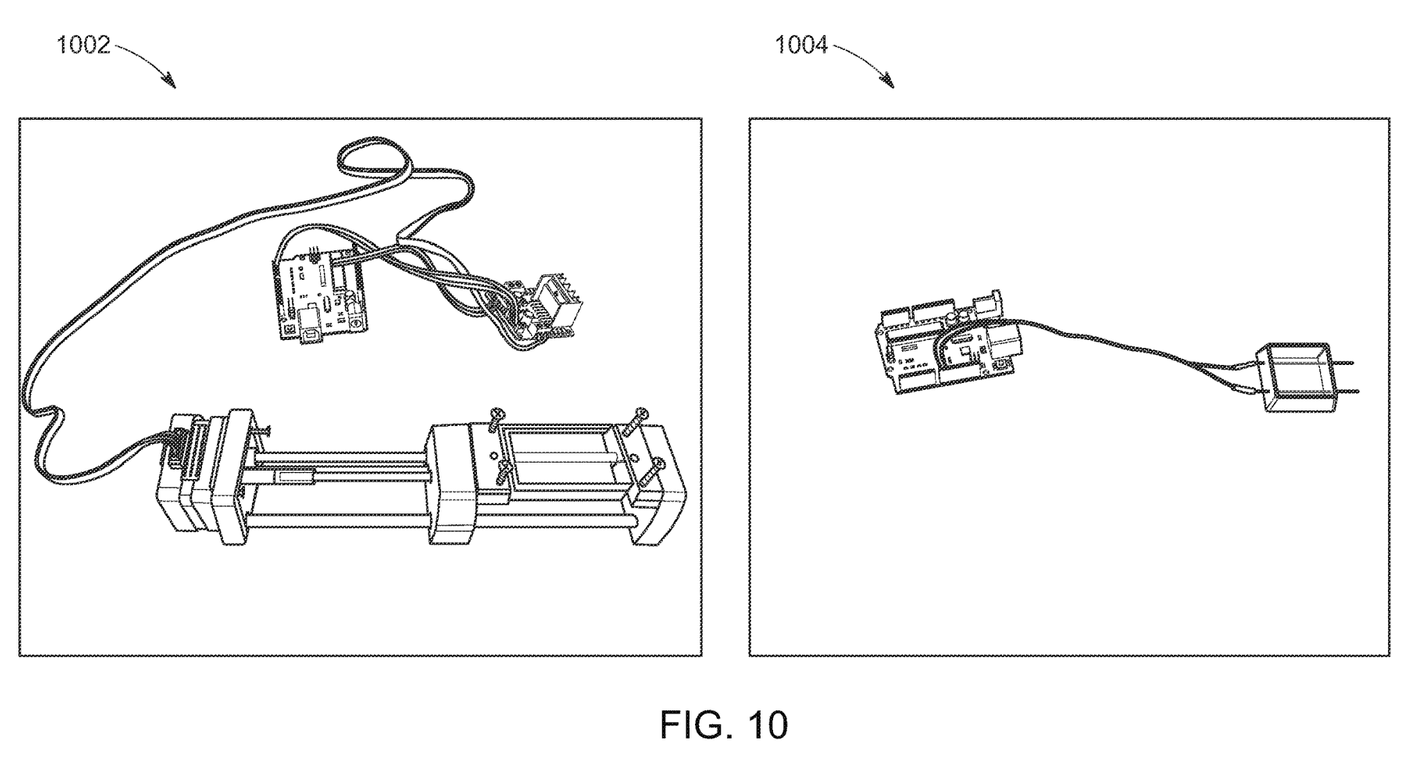
FIG. 10 depicts images of a first mechanical stimulation scenario and a second electrical stimulation scenario, according to at least some embodiments disclosed herein.

Cells constantly receive dynamic cues in in vivo conditions. These cues include electrical and/or mechanical stimulation. Recreating such cues in the in vitro conditions can be used to guide cellular behavior including cell alignment, ECM production, and even differentiation path of the stem cells to different cell types. It is possible to apply mechanical stimulation to the cells grown on the PDMS membrane by stretching or compressing the membrane that is flexible. Electrodes can also be inserted inside the bulk of the membrane close to the surface or above the surface to apply electrical stimulation to the cells. FIG. 10 depicts a first mechanical stimulation 1002 scenario and a second electrical stimulation scenario 1004.

Patterning Different Cell Types

Figure 11:
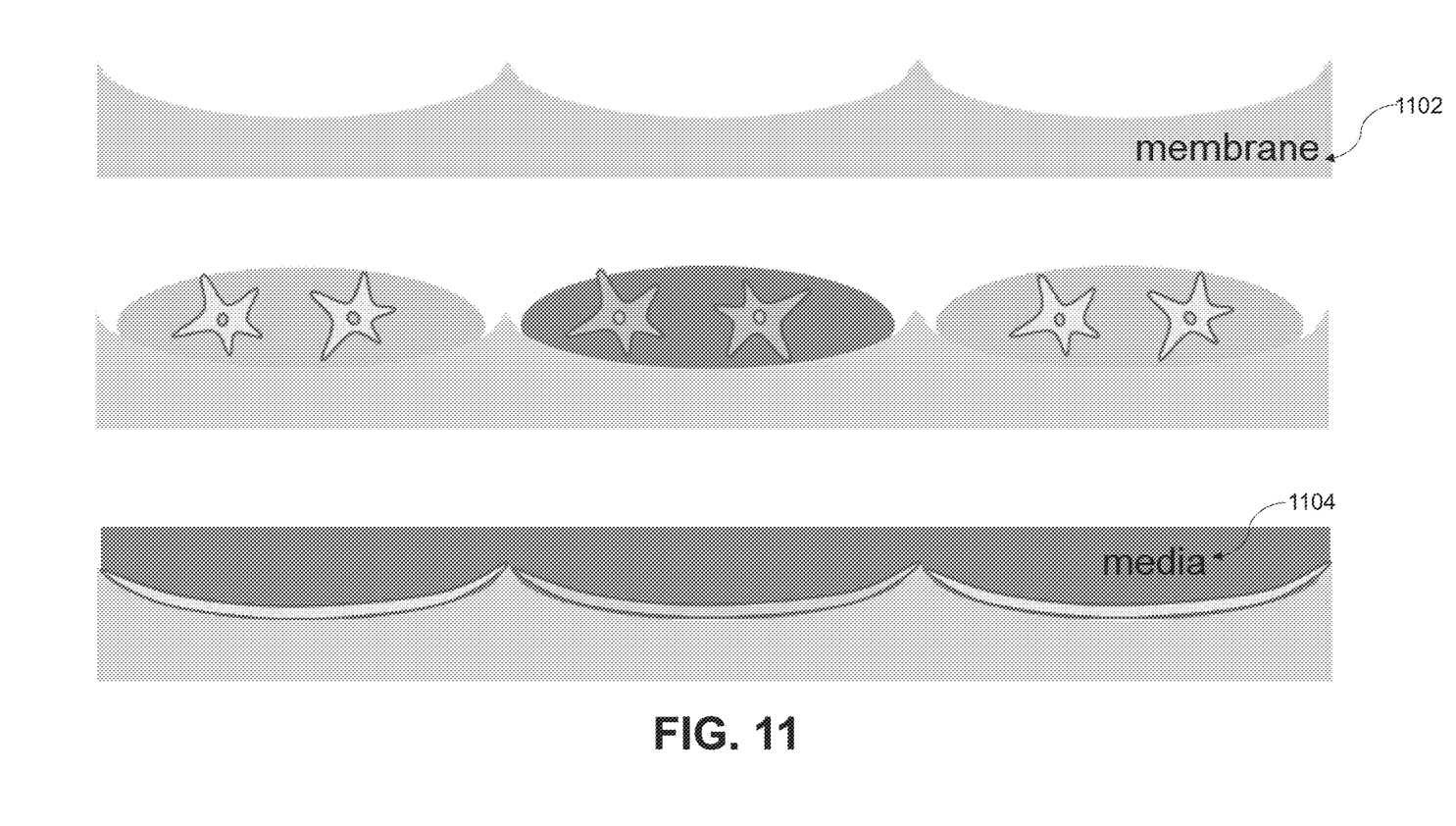
FIG. 11 depicts a schematic diagram of grooves and concave shapes created from patterns on a surface of the silicone-based membrane such that these and concave shapes are fillable with different cell types and cell culture media for purposes of positioning different cell types, according to at least some embodiments disclosed herein.

The patterns created on the surface of the membrane 1102 of FIG. 11 creates grooves with concave shapes. Although the depth of these grooves are not much bigger than the size of the cells themselves and they can still cover the whole surface uniformly, this feature can be used to pattern different cell types on the PDMS membrane 1102. Each of these concave grooves can be filled with a low volume of cell culture media 1104 of FIG. 11 with a certain cell type in a way that the solutions in adjacent grooves do not touch each other. After a short amount of time (e.g., a time period of about thirty minutes to about sixty minutes), cells adhere to the surface of the groove and extra media 1104 can be added to cover the whole surface. This can be used to position different cell types on different locations of each PDMS membrane 1102. For example, by patterning fat and muscle cells, it is possible to create marbling for cultivated meat application.

Decellularized Cell Sheets as Fibrous Scaffolding

After the sheets are formed by delaminating the cell and the ECM layer, since there is a high content of ECM present, the sheets can be decellularized using mild detergents such as Triton X-100, SDS, or Tween 20, at room temperature for a short time or on ice for longer times. After decellularization, a fibrous sheet of rich ECM will remain that can be used for 3D cell culture in vitro or in vivo regenerative medicine and tissue engineering applications. The ECM sheets can also be treated with DNase and RNases to remove any DNA and RNA residues. By using different cell types or treating them with different types of media, the composition of ECM can be controlled. Membrane surface patterns, as well as external stimuli including electrical and mechanical stimuli, can be used to align the ECM components in certain directions, as described herein. Further crosslinking of the ECM proteins, before or after decellularization can also be performed. The directionality of ECM will be preserved during decellularization and can guide cellular behavior after re-cellularization.

Solubilized ECM

The decellularized ECM can also be solubilized to create liquid ECM that can be used for surface treatment or 3D cell culture. The decellularized ECM can be solubilized using a high ionic strength solution, such as 3-4 molar urea solution in deionized water or by treating it with enzymes such as Pronase, Dispase, or different collagenases or their combinations. Sonication and homogenization can be performed to help with solubilization. It should be appreciated that these processes are performed on ice. After solubilization, the solution is filtered using dialysis filters to remove the enzymes or ionic solution. It can then be lyophilized and solubilized again in the deionized water to achieve the desired concentration. This solution can then be kept refrigerated or frozen until use. The potential applications for this include treatment of surfaces that are not suitable for cell attachment to render them cell adhesive or 3D culture systems using "cell-derived ECM" as the main matrix. This solution is temperature sensitive and can be gelled quickly in a few minutes by increasing the temperature to a temperature of about 37° C.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

When introducing elements of the present disclosure or the embodiments thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and scope of the invention.

REFERENCES

The following references, to the extent that they provide exemplary procedural or other details supplementary to those set forth herein, are specifically incorporated herein by reference.

Chakrabarty, T., et al., "Bioinspired tannic acid-copper complexes as selective coating for nanofiltration membranes," Separation and Purification Technology, 2017. 184: 188-94.

Chuah, Y. J., et al., "Simple surface engineering of polydimethylsiloxane with polydopamine for stabilized mesenchymal stem cell adhesion and multipotency," Scientific Reports, 2015. 5(1): 18162.

Fritz, J. L. and M. J. Owen, "Hydrophobic Recovery of Plasma-Treated Polydimethylsiloxane," The Journal of Adhesion, 1995. 54(1-4): 33-45.

Guillaume-Gentil, O., et al., "pH-controlled recovery of placenta-derived mesenchymal stem cell sheets," Biomaterials, 2011. 32(19): 4376-84.

Li, Q., et al., "Polydopamine-collagen complex to enhance the biocompatibility of polydimethylsiloxane substrates for sustaining long-term culture of L929 fibroblasts and tendon stem cells," Journal of Biomedical Materials Research Part A, 2018. 106(2): 408-18.

Lv, X., et al., "A one-step tannic acid coating to improve cell adhesion and proliferation on polydimethylsiloxane," New Journal of Chemistry, 2020. 44(35): 15140-47.

Owaki, T., et al., "Cell sheet engineering for regenerative medicine: current challenges and strategies," Biotechnol J, 2014. 9(7): 904-14.

Shahin-Shamsabadi, A. and P. R. Selvaganapathy, "it-SACS: pH Induced Self-Assembled Cell Sheets Without the Need for Modified Surfaces," ACS Biomater Sci Eng, 2020. 6(9): 5346-56.

Sharma, V., et al., "Surface characterization of plasma-treated and PEG-grafted PDMS for micro fluidic applications," Vacuum, 2007. 81(9): 1094-1100.

Walsh, D. I., et al., "Enabling Microfluidics: from Clean Rooms to Makerspaces," Trends in Biotechnology, 2017. 35(5): 383-92.

Wu, M.-H., "Simple poly(dimethylsiloxane) surface modification to control cell adhesion," Surface and Interface Analysis, 2009. 41(1): 11-16.

Yamada, N., et al., "Thermo-responsive polymeric surfaces; control of attachment and detachment of cultured cells," Die Makromolekulare Chemie, Rapid Communications, 1990. 11(11): 571-76.

What is claimed is:

1. A method to create a cell sheet, the method comprising:
   treating a silicone-based membrane with an aqueous solution, wherein the silicone-based membrane comprises a polydimethylsiloxane (PDMS) elastomer;
   growing cells on the treated membrane;
   aligning the cells on the treated membrane; and
   creating a cell sheet.

2. The method of claim 1, wherein the aqueous solution is selected from the group consisting of: an aqueous solution of tannic acid and an aqueous solution of lignin.

3. The method of claim 2, wherein the membrane is treated directly with about 50 mg/mL of the aqueous solution of tannic acid or about 1 mg/mL of the aqueous solution of lignin at room temperature for a time period of about 3 days.

4. The method of claim 2, further comprising:
   treating the surface of the membrane with plasma or air atmosphere to improve a wettability of the surface of the membrane.

5. The method of claim 2, further comprising:
   penetrating the surface of the treated membrane with a solution to improve a wettability of the surface of the membrane.

6. The method of claim 5, wherein the solution comprises a sodium hydroxide solution in deionized water.

7. The method of claim 1, wherein the aligning of the cells on the treated membrane occurs by creating patterns on a surface of the treated membrane via lithography.

8. The method of claim 1, wherein the aligning of the cells on the treated membrane occurs by creating protein patterns on the surface of the treated membrane.

9. The method of claim 1, wherein the aligning of the cells on the treated membrane occurs by utilizing three-dimensional (3D) printing to create patterns that can be replicated to the treated membrane by casting.

10. The method of claim 9, wherein the 3D printing comprises Fused Deposition Modeling (FDM) 3D printing.

11. The method of claim 9, wherein the patterns are used as topographical signaling cues for the cells that are smaller to be aligned in certain directions.

12. The method of claim 11, wherein each pattern of the patterns is selected from the group consisting of a parallel pattern, a circular pattern, and a concentric pattern.

13. The method of claim 9, further comprising:
   determining that the cells are confluent and have produced the predetermined amount of ECM.

14. The method of claim 13, further comprising:
   growing additional cells on a cell-ECM layer.

15. The method of claim 13, further comprising:
   cross-linking the predetermined amount of ECM produced by the cells with tannic acid or lignin to create a stable structure.

16. The method of claim 15, further comprising:
   wherein the creating the cell sheet step comprises removing the cells and ECM of the cells from the surface of the membrane.

17. The method of claim 16, wherein removal of the cells and the ECM of the cells from the surface of the membrane occurs by scraping the cells and the ECM of the cells off of the surface of the membrane.

18. The method of claim 1, further comprising:
   inducing the cells to produce a sufficient of extracellular matrix (ECM) by treating the cells with an ascorbate.

19. The method of claim 1, further comprising:
   inducing the cells to produce a sufficient of extracellular matrix (ECM) by adding a polyethylene glycol (PEG) or carrageenan to media.

20. The method of claim 1, further comprising:
   washing and autoclaving the treated membrane to reuse the treated membrane to grow new cells.

* * * * *